(12) United States Patent
Reed et al.

(10) Patent No.: US 9,776,947 B2
(45) Date of Patent: Oct. 3, 2017

(54) PROCESS FOR THE PRODUCTION OF DIALKYL SUCCINATE FROM MALEIC ANYHDRIDE

(71) Applicant: Johnson Matthey Davy Technologies Limited, London (GB)

(72) Inventors: Graham Reed, London (GB); Andrew George Hiles, London (GB); Rikard Umberto Andersson, London (GB); Simon Nicholas Tilley, Thronaby (GB); Paul Gordon, Thornaby (GB)

(73) Assignee: JOHNSON MATTHEY DAVY TECHNOLOGIES LIMITED, London (GB)

( * ) Notice: Subject to any disclaimer, the term of this patent is extended or adjusted under 35 U.S.C. 154(b) by 53 days.

(21) Appl. No.: 14/431,408

(22) PCT Filed: Oct. 13, 2014

(86) PCT No.: PCT/GB2014/053075
§ 371 (c)(1),
(2) Date: Mar. 26, 2015

(87) PCT Pub. No.: WO2015/055992
PCT Pub. Date: Apr. 23, 2015

(65) Prior Publication Data
US 2016/0214922 A1 Jul. 28, 2016

(30) Foreign Application Priority Data
Oct. 14, 2013 (GB) .................................. 1318175.5

(51) Int. Cl.
*C07C 67/08* (2006.01)
(52) U.S. Cl.
CPC .................................. *C07C 67/08* (2013.01)
(58) Field of Classification Search
CPC ...... C07C 67/08; C07C 67/303; C07D 307/60
See application file for complete search history.

(56) References Cited

U.S. PATENT DOCUMENTS

| | | | |
|---|---|---|---|
| 2,772,292 A | 11/1956 | McShane, Jr. et al. | |
| 2,772,293 A | 11/1956 | Gilbert et al. | |
| 2,975,218 A | 3/1961 | Buchner et al. | |
| 3,361,832 A | 1/1968 | Pine et al. | |
| 3,830,830 A | 8/1974 | Cleveland et al. | |
| 4,010,197 A | 3/1977 | Toriya et al. | |
| 4,032,458 A | 6/1977 | Cooley et al. | |
| 4,155,919 A | 5/1979 | Couteau et al. | |
| 4,268,695 A | 5/1981 | Lange et al. | |
| 4,550,185 A | 10/1985 | Mabry et al. | |
| 4,562,283 A | 12/1985 | Schnabel et al. | |
| 4,584,419 A | 4/1986 | Sharif et al. | |
| 4,609,636 A | 9/1986 | Mabry et al. | |
| 4,656,297 A | 4/1987 | Kouba et al. | |
| 4,751,334 A | 6/1988 | Turner et al. | |
| 4,767,869 A | 8/1988 | Harrison et al. | |
| 4,792,620 A * | 12/1988 | Paulik .................. | B01J 31/0231 560/232 |
| 4,810,807 A | 3/1989 | Budge et al. | |
| 4,919,765 A | 4/1990 | Wilkes et al. | |
| 4,940,805 A | 7/1990 | Fischer et al. | |
| 4,945,173 A | 7/1990 | Wood | |
| 4,985,572 A | 1/1991 | Kitson et al. | |
| 5,073,650 A * | 12/1991 | Stabel .................. | C07C 29/177 568/864 |
| 5,196,602 A | 3/1993 | Budge et al. | |
| 5,254,758 A | 10/1993 | Hiles et al. | |
| 5,310,954 A | 5/1994 | Hiles et al. | |
| 5,606,099 A | 2/1997 | Darsow | |
| 5,698,749 A | 12/1997 | Pedersen et al. | |
| 5,872,276 A | 2/1999 | Darsow | |
| 5,969,164 A | 10/1999 | Budge et al. | |
| 6,008,384 A | 12/1999 | Bockrath et al. | |
| 6,495,730 B1 | 12/2002 | Konishi et al. | |
| 6,989,455 B2 | 1/2006 | Hepfer et al. | |
| 7,154,011 B2 | 12/2006 | Hesse et al. | |
| 7,169,958 B2 | 1/2007 | Hesse et al. | |
| 7,271,299 B2 | 9/2007 | Hesse et al. | |
| 7,598,404 B2 | 10/2009 | Backes et al. | |

FOREIGN PATENT DOCUMENTS

| | | |
|---|---|---|
| CN | 101343211 A | 1/2009 |
| CN | 102070448 A | 5/2011 |
| CN | 102863335 A | 1/2013 |
| DE | 1901870 A1 | 9/1969 |
| DE | 2321101 A1 | 11/1974 |
| DE | 2543673 A1 | 4/1976 |
| DE | 2519817 A1 | 11/1976 |
| EP | 0382050 A1 | 8/1990 |
| GB | 1226292 A | 3/1971 |
| GB | 1454440 A | 11/1976 |
| GB | 1551741 A | 8/1979 |
| HU | 41727 * | 5/1985 |
| JP | H01216958 A | 8/1989 |
| JP | H0491055 A | 3/1992 |
| WO | 8603189 A1 | 6/1986 |
| WO | 8800937 A1 | 2/1988 |
| WO | 9101960 A1 | 2/1991 |
| WO | 9935113 A2 | 7/1999 |
| WO | 03006446 A1 | 1/2003 |
| WO | 2005058855 A1 | 6/2005 |
| WO | 2011017543 A1 | 2/2011 |

OTHER PUBLICATIONS

International Search Report and Written Opinion for PCT/GB2014/053075 dated Jan. 14, 2015.
International Preliminary Report on Patentability for PCT/GB2014/053075 dated Apr. 28, 2016, 7 pages.

* cited by examiner

Primary Examiner — Paul A Zucker
(74) Attorney, Agent, or Firm — Armstrong Teasdale LLP

(57) ABSTRACT

In a process for the production of dialkyl succinate from a feedstock comprising maleic anhydride, feed in the liquid phase is provided to a reactor operated at a temperature of at least about 150° C. The feed is contacted with hydrogen at a pressure of at least about 300 psig in the presence of an acid tolerant catalyst and an alkanol wherein at least some of the carbon carbon double bonds of the maleic anhydride are hydrogenated to form succinic acid and that the heat generated promotes esterification to dialkyl succinate in situ. A stream of dialkyl succinate is recovered from the reactor.

8 Claims, 2 Drawing Sheets

PROCESS FOR THE PRODUCTION OF DIALKYL SUCCINATE FROM MALEIC ANYHDRIDE

The present invention relates to a process for the production of dialkyl succinate from a feedstock comprising maleic anhydride.

It is known to produce diols by reaction of dicarboxylic acids and/or anhydrides, or mono or di-alkyl esters, lactones, and mixtures thereof with hydrogen. Commercially, where the desired product is 1,4-butanediol, typically with the co-products tetrahydrofuran and γ-butyrolactone, the starting material is normally a dialkyl ester of maleic acid and/or anhydride, such as dimethyl maleate or diethyl maleate, which may contain minor amounts of dialkyl fumarate and/or dialkyl succinate.

Information relating to these processes can be found in, for example, U.S. Pat. No. 4,584,419, U.S. Pat. No. 4,751,334, WO86/03189, WO88/00937, U.S. Pat. No. 4,767,869, U.S. Pat. No. 4,945,173, U.S. Pat. No. 4,919,765, U.S. Pat. No. 5,254,758, U.S. Pat. No. 5,310,954 and WO91/01960.

The dialkyl maleates which are used as feedstock in these conventional reaction processes may be produced by any suitable means. The production of dialkyl maleates for use in such processes is discussed in detail in U.S. Pat. No. 4,584,419, U.S. Pat. No. 4,751,334 and WO88/00937.

In one conventional process for the production of 1,4-butanediol and co-product tetrahydrofuran with optional production of γ-butyrolactone, a dialkyl ester, such as dimethyl maleate together with any residual methanol from the esterification reactor, is fed to a vaporiser where it is vaporised by a stream of hot cycle gas fed to the vaporiser. The hot cycle gas stream may be mixed with make-up hydrogen. The cycle gas will normally contain a high concentration of hydrogen gas but may also include other gases including hydrocarbons, carbon oxides, methane and nitrogen. Further, where the cycle gas includes recycled gases from downstream, condensables, including product ether, methanol, water, co-products, and by-products, may also be present.

The combined vaporous stream from the vaporiser is then passed to a reactor where it is reacted to form 1,4-butanediol, tetrahydrofuran and/or γ-butyrolactone. The product stream is cooled and the reaction products are condensed and separated from the excess cycle gas before being passed to a refining zone. In the refining zone the various products are separated and the 1,4-butanediol and the tetrahydrofuran are removed. The γ-butyrolactone, together with the intermediate dimethyl succinate and some 1,4-butanediol, may be recycled. In one arrangement the γ-butyrolactone may be at least partially extracted in an optional refining zone and recovered. The methanol water stream separated from the product mix will be recycled upstream. In general, a significant portion of the 1,4-butanediol produced by this or other conventional methods is subsequently converted to tetrahydrofuran.

Figure 2:
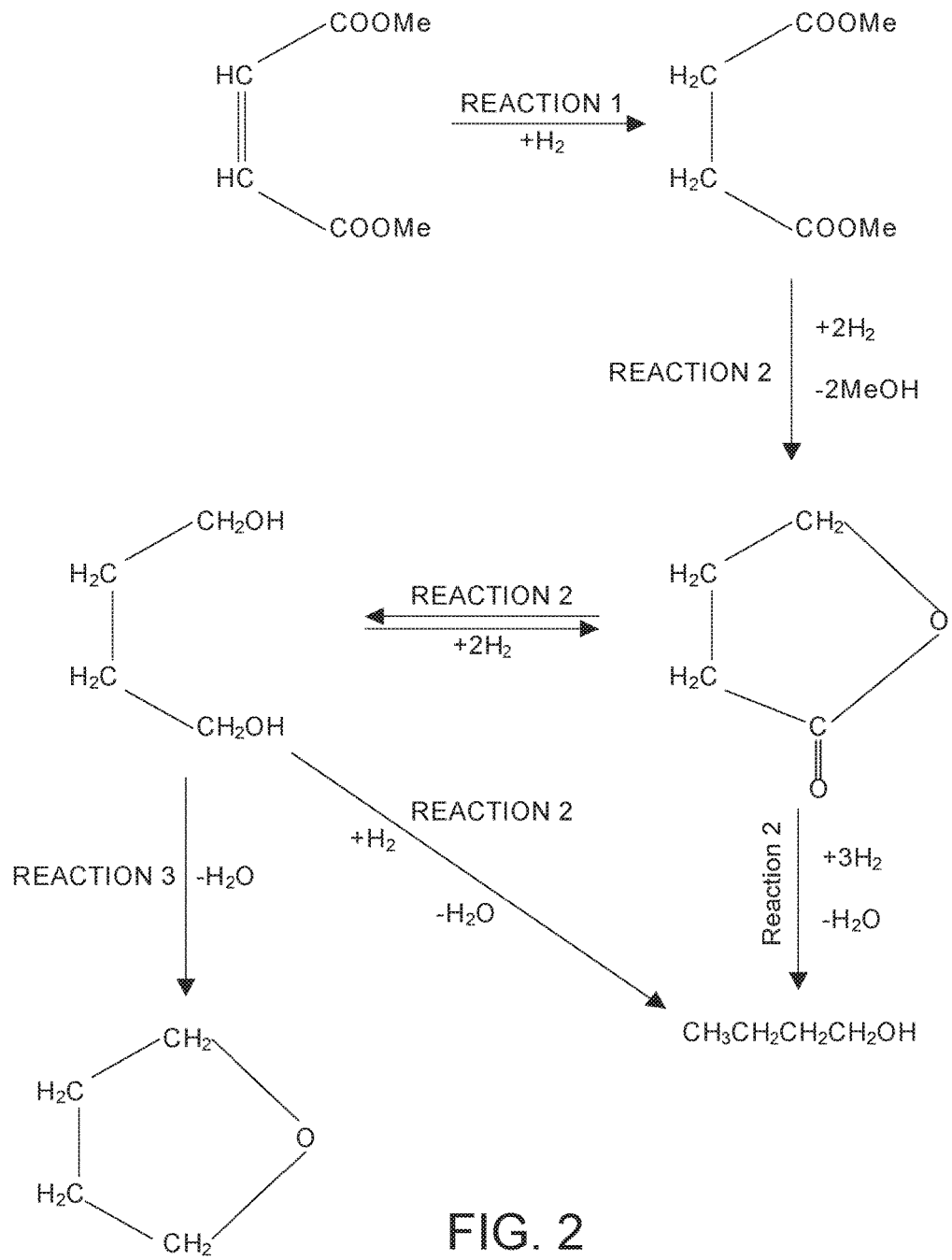

The overall reaction which occurs is a series of steps and includes a final dehydration step in which the tetrahydrofuran is produced. A probable reaction path is set out in Scheme 1, which is illustrated in FIG. 2.

Reaction 1 may be regarded as hydrogenation of the ester (and is a reaction of the carbon/carbon double bond), Reaction 2 may be regarded as hydrogenolysis (and is a reaction of the saturated ester to butanediol, γ-butyrolactone and by-product butanol) and Reaction 3 may be regarded as dehydration (and is a reaction of butanediol to tetrahydrofuran).

An alternative process is described in WO99/35113 in which maleic anhydride esters are fed to a reaction process in which three different catalysts are used. First the maleate is converted to the succinate in the presence of the first catalyst, which is a heterogeneous selective hydrogenation catalyst, at a temperature of from 120° C. to 170° C. and a pressure of from 3 to 40 bara. The succinate is then passed directly to the presence of the second catalyst where it is converted mainly into γ-butyrolactone. The product of the reaction with the second catalyst is then fed directly to the presence of a third catalyst which is used to dehydrate the γ-butyrolactone to produce tetrahydrofuran. Some of the γ-butyrolactone formed in the presence of the second catalyst is transferred to a second reaction loop operating at a higher pressure where it is converted to 1,4-butanediol.

As the first step in Scheme 1 and the first catalyst used in the alternative process described in WO99/35113 relates to the hydrogenation of the dimethyl maleate to dimethyl succinate, it has been suggested that dimethyl succinate or diethyl succinate may be suitable starting materials for the reaction with hydrogen to form 1,4-butanediol, tetrahydrofuran and/or γ-butyrolactone.

One process in which dimethyl succinate is used in the production of tetrahydrofuran and 1-4-butanediol is described in U.S. Pat. No. 4,656,297. In this process, methanol is added to the ester feed to increase conversion and reduce transesterification. Another example of a process in which dimethyl succinate is suggested as a feed is WO99/35136 in which reaction with hydrogen occurs over two different catalysts, to form a mixture of tetrahydrofuran and γ-butyrolactone.

An alternative process is described in WO03/006446 in which feed material selected from mono-esters of unsaturated dicarboxylic acids and/or anhydrides, diesters of unsaturated dicarboxylic acids and/or anyhydrides, unsaturated lactones, and mixtures of two or more thereof is reacted with hydrogen. This process comprises the steps of:
  (a) vaporising the organic feed material in a vapourising zone into the hydrogen containing stream to form an organic feed material carrying hydrogen stream;
  (b) contacting the organic feed material carrying hydrogen stream with a catalyst in a vaporiser, said vaporiser operating under reaction conditions such that at least some of the carbon carbon double bonds are saturated;
  (c) supplying the hydrogen-containing stream containing the vaporised at least partially saturated feed to a reaction zone comprising catalyst and operating under reaction conditions; and
  (d) recovering from the reaction zone a product stream comprising an ether and/or diol and/or a lactone.

Whilst this process successfully provides the desired products, and offers an improved process in terms of economics and efficiency over earlier processes, it is desirable to further improve the economics and efficiency of the process.

An improved process is described in WO2005/058855 in which it is intended to minimise the cycle gas requirements and minimising the production of unwanted by-product. The described process comprises the steps of:
  (a) supplying a stream comprising at least a portion of the organic feed material selected from mono-esters of unsaturated dicarboxylic acids and/or anhydrides, diesters of unsaturated dicarboxylic acids and/or anhydrides, unsaturated lactones and mixtures of two or more thereof in the presence of hydrogen to a pre-reactor zone comprising catalyst and operating under reaction conditions and contacting said feed with a hydrogen containing stream such that at least some of the carbon carbon double bonds are saturated;

(b) vaporising the at least partly saturated feed into the hydrogen containing stream in a vaporising zone;

(c) supplying the hydrogen-containing stream containing the vaporised at least partially saturated feed to a reaction zone comprising catalyst and operating under reaction conditions;

(d) recovering from the reaction zone a product stream comprising the ether and optionally diol and/or lactone; and (e) recycling depleted hydrogen-containing stream to at least the pre-reactor zone or the vaporisation zone.

Thus, in some of these processes at least some of the unsaturated ester is saturated in a pre-reactor before being vaporised into the hydrogen-containing stream and then subjected to the hydrogenolysis reaction.

One alternative process has been described in WO2011/017543. In this process, the dialkyl succinate is formed from co-products or residues obtained from maleic anhydride manufacture rather than from the maleic ester. The process comprises: (a) providing a mixture comprising about 30 to 90 wt % maleic anhydride and about 5 to 68 wt % fumaric acid; (b) contacting the mixture of (a) with an alkyl alcohol solvent in a sufficient amount to form a solution and holding the solution at a temperature of from 20° C. to about 250° C. for a holding time; (c) hydrogenating the solution of (b), in the absence of an intermediate distillation between (b) and (c), at hydrogenation conditions of temperature of about 50° C. to 200° C. under hydrogen pressure from about 50 to 1000 psig (about 450 to 7000 kPa) in the presence of a hydrogenation catalyst to form a hydrogenation product; (d) treating the hydrogenation product with alcohol at an esterification temperature of about 100° C. to 140° C. to form crude product containing dialkyl esters, wherein at least 85% of maleic anhydride, fumaric acid and their derivatives of (a) have been converted to dialkyl esters in the crude product; and (e) isolating dialkyl esters from the crude product of (d).

Whilst these various processes offer means for obtaining the desired products, they each suffer from various disadvantages and drawbacks.

In many of the known processes, a copper based catalyst may be used for the hydrogenation reaction. However, acidic species will deactivate these catalysts necessitating regular shut down to replace deactivated catalyst. This deactivation may be exacerbated by the high heat release on the conversion of the double bond in the hydrogenation step.

A further problem is that it can be difficult to separate by distillation the acidic species in processes utilising dialkyl maleates. This is due to the reversion of the diester to the maleic anhydride which yields close boiling compounds. To address this problem, high conversion of the acidic species to diesters in the reaction system before vaporisation is required. This increases the physical size of the reaction column required to achieve the necessary high conversion.

A particular problem relates to the formation of insoluble fumarates in the alkyl maleate system. To attempt to minimise fumarate formation, it is necessary to restrict the temperature of the esterification reaction. The lower temperature means that a catalyst has to be used.

In addition, the requirement for high conversion of the mono-alkyl maleate to the di-alkyl maleate requires a large excess of dry methanol to complete the reaction. This has the disadvantage of requiring a high energy input and equipment costs to recover dry methanol by distillation such that it can be recycled.

A still further problem associated with the conventional reaction processes is that by-products may be formed by reaction across the double bond. By-products conventionally formed include hydroxyl dialkyl succinate.

An additional problem with these prior art processes is that dialkyl maleates, such as dimethyl maleate) vaporised in hydrogen, is less volatile than the corresponding succinate and thus more hydrogen is required to vaporise the feed which increases the size of the equipment required for the hydrogenation step.

Whilst utilising aqueous maleic acid as feed might be considered desirable as addressing some of the above problems, it would be necessary to remove any water present. However, this removal process may lead to the formation of fumaric acid with its attendant problems and hence require the use of more expensive equipment and a high energy cost to dehydrate aqueous maleic acid to dry feed maleic anhydride for the esterification reaction.

Where the process includes a recycle, 1,4-butanediol, and/or γ-butyrolactone may be present in the recycle stream. These compounds can react with the dialkyl maleate to form long chain oligomers. These can grow in the vaporiser and at the inlet to the catalyst bed to form a "polymer". The presence of the polymer may result in the need to shut down the hydrogenation reactor prematurely to remove the polymer. Polymers may also be formed by cross linking of the double bonds in the maleates.

Where a process requires the hydrogenation of maleic acid to succinic acid prior to esterification, the presence of the acid species can lead to deactivation of the catalyst. In addition they will cause corrosion problems unless high grade expensive materials are used for the construction of the reactors. Additionally or alternatively the temperature at which the reactor is operated may have to be limited. Further, carrying out hydrogenation of maleic acid to succinic acid may result in operating problems due to the insolubility and high freezing points of the components.

It is therefore desirable to provide an alternative process which addresses at least one of these problems.

It has now been found that by carrying out the pre-saturation of the double bond prior to the esterification but in the same reactor, the heat generated by the saturation will allow the esterification reaction to occur without the need for a catalyst. That is to say that the esterification reaction is auto-catalysed.

Thus according to a first aspect of the present invention there is provided a process for the production of dialkyl succinate from a feedstock comprising maleic anhydride, said process comprising the steps of:

(a) providing the feed in the liquid phase to a reactor operated at a temperature of at least about 150° C.;

(b) contacting said feed with hydrogen at a pressure of at least about 300 psig in the presence of an acid tolerant catalyst and an alkanol wherein at least some of the carbon carbon double bonds of the maleic anhydride are hydrogenated to form succinic acid and that the heat generated promotes esterification to dialkyl succinate in situ; and (c) recovering a stream comprising dialkyl succinate from the reactor.

Thus the heat generated by the hydrogenation of the double bond can be utilised to promote the esterification reaction. In one arrangement, the heat generated may be sufficient to enable the esterification reaction to be carried out in the absence of a catalyst and hence the problems associated with the life expectancy of the esterification catalyst in prior art processes are obviated. In one alternative arrangement, an esterification catalyst may be used. In a further alternative arrangement, a combined catalyst may be used.

For the avoidance of doubt, the esterification part of the reaction is carried out in the same reactor as the hydrogenation of the double bond. Whilst cooling may be provided in the reactor to control the exotherm, this is not generally preferred and the temperature will be maintained at least about 150° C. The heat generated during the hydrogenation may advantageously drive off the water from the product succinate. This will be assisted where the alkanol is methanol and is present in excess.

Generally any unesterified anhydride or acid species remaining in the stream recovered at step (c) will be in the saturated form and so will be succinic anhydride or succinic acid.

It should be noted that some monoesterification of the maleic acid or anhydride may occur within the reaction vessel prior to the saturation reaction occurring without departing from the scope of the present invention.

The present invention offers significant advantages over the various prior art processes. For example, any acidic monoalkyl succinate, such as monomethyl succinate, and any succinic acid remaining in the stream recovered in step (c) are easier to separate from the dialkl succinate, such as dimethyl succinate, than the separation of the corresponding maleic/maleate species. In one arrangement of the present invention, a bottom liquid stream from the separator may be recycled to the hydrogenation/esterification reactor. The size of the reaction column is therefore greatly reduced. This in turn will reduce the capital and operating costs.

In some arrangements, a polishing esterification reaction may additionally be required to esterify any remaining succinic acid or any monoalkyl succinic acid in stream recovered in step (c) but this will generally be of a smaller size than has been required heretofore.

The saturation of the double bond prior to esterification reduces the likelihood of by-products such as alkoxy dialkyl succinate and hydroxyl dialkyl succinate forming in the esterification reaction and thus an overall yield improvement will generally be noted. In addition, the saturation of the carbon carbon double bond reduces the risk of isomerisation to the fumarate occurring.

The present invention enables the reaction to operate at a lower conversion rate. This enables a lower quantity of alkanol to be used than is required in conventional processes. In conventional processes, the conversion is typically at least 99%. The present invention can be operated at as low as 50% conversion but it will preferably be operated at about 80 to 90% conversion to the dialkly succinate.

In addition, alkanol having a higher water content than has been usable heretofore may be used. In conventional processes essentially dry alkanol is required. Thus where methanol is used, it will conventionally be required to have a water content of less than 0.05 wt %. In the process of the present invention where methanol is the alkanol a higher water content of about 1 to about 2% or even higher may be used. The feed to the reactor will generally comprise at least 90% maleic anhydride. In one arrangement, a feed comprising 92 to 95% maleic anhydride may be used. In an alternate arrangement, a feed comprising 97, 98, 99, 99.5, 99.8 or 100% maleic anhydride may be used.

Any suitable alkanol may be used. Generally a $C_1$ to $C_4$ alkanol will be used with methanol or ethanol being particularly preferred.

The saturation reaction may be carried out at any suitable temperature provided that it is at least 150° C. In one arrangement, a temperature in the range of from about 150° C. to about 240° C. may be used although higher temperatures may also be used. Other suitable temperatures include those of 155° C., 160° C., 170° C., 180° C., 190° C., 200° C., 210° C., 220° C. and 230° C. As there is no possibility of insoluble fumarates being formed, higher temperatures can be utilised than is conventional. This will enable a reduced size of reactor to be used which in turn will reduce the associated costs.

Any suitable pressure may be used provided that the alkanol is kept in liquid phase at the high temperatures generated by the exotherm of the hydrogenation reaction. In one arrangement, a hydrogen pressure of about 300 psig to about 900 psig will be used. Suitable hydrogen pressures include 400 psig, 500 psig, 600 psig, 700 psig and 800 psig.

Any suitable catalyst may be used for the hydrogenation reaction. In one arrangement a heterogeneous catalyst may be used. Palladium catalysts may offer some advantages. The catalyst may be provided on a suitable support. In one arrangement, a palladium on carbon catalyst may be used. Other suitable catalysts include supported palladium. Where a combined catalyst is used for the hydrogenation and the esterification, any suitable catalyst such as palladium supported on alumina.

Any suitable flow through rate may be used. In one arrangement a residence time of about 10 to about 60 minutes will be suitable.

The product diester succinate, such as dimethyl succinate, has a lower vapour pressure than the corresponding maleate, and this, together with the fact that the heat generated is used in the esterification reaction thereby managing the exotherm across the hydrogenation bed means that the throughput of feed to the hydrogenation bed can be increased. In one arrangement, this can be achieved in the manner described in WO 2005/058855 which is incorporated herein by reference.

In addition, the hydrogenation of aqueous maleic acid to succinic acid prior to esterification eliminates the need to remove the water in the generation of maleic anhydride. Without the need to control the temperature or the problems associated with insoluble fumarates formation that are associated with the maleate system, the reaction can be operated at temperatures leaving a molten stream of succinic acid.

Any monoalkyl succinate formed in the reaction may be recycled to the reactor. In one arrangement, the monoalkyl succinate may be recovered with the dialkyl succinate and will then be separated before being recycled. In an alternate arrangement, the reaction, separation of monoalkyl succinate and recycle to the reaction may be carried out in the same vessel.

Figure 1:
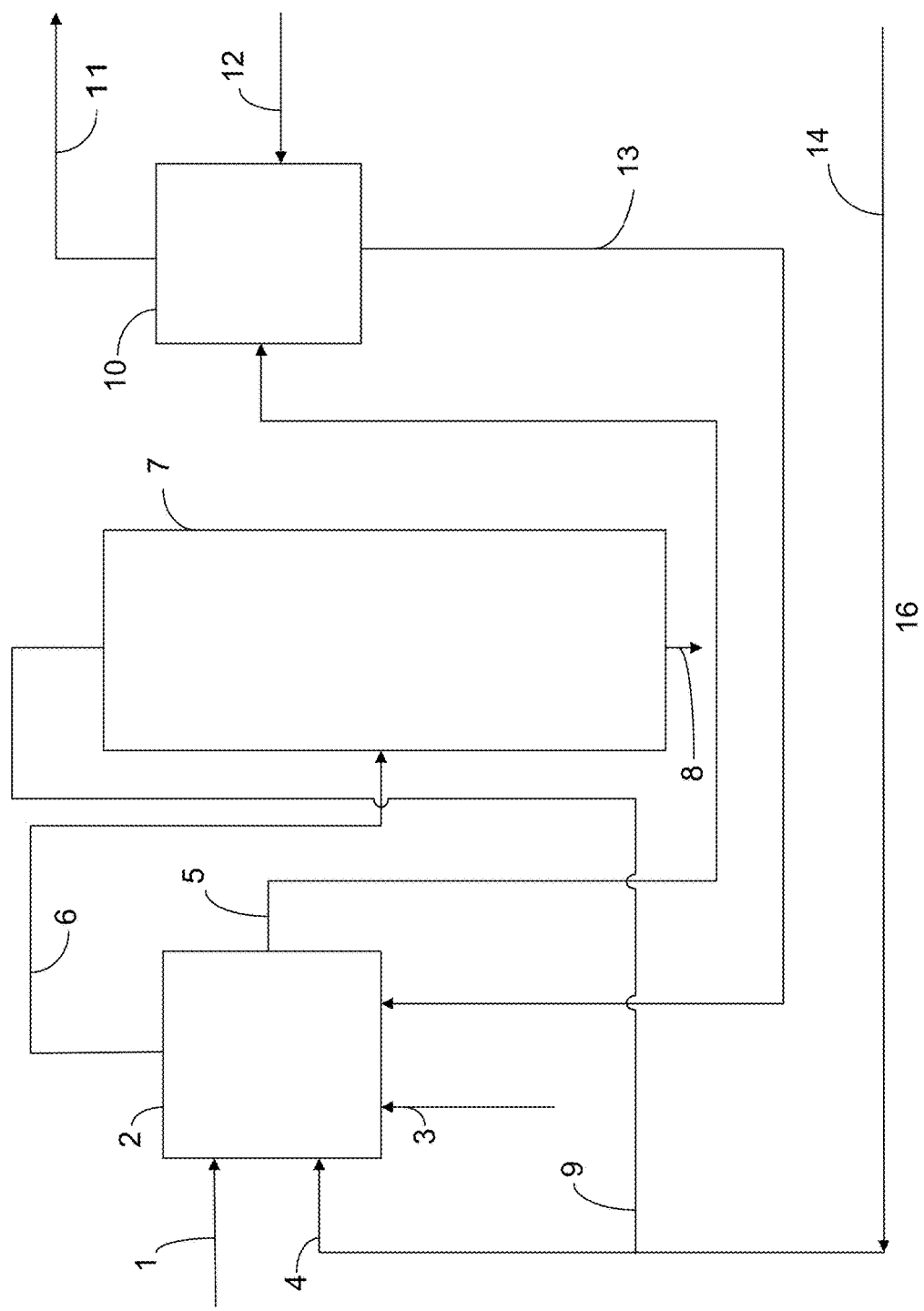

The present invention will now be described by way of example with reference to the accompanying drawings in which:

FIG. 1 is a schematic illustration of a flow sheet according to the present invention FIG. 2 is Scheme 1 illustrating a reaction path according to the present invention It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

The invention will be discussed with reference to the methylation of maleic anhydride. However, it is equally applicable to the use of other alkanols.

Maleic anhydride is fed in line 1 to the reactor 2 containing a hydrogenation catalyst and operating under hydrogenation conditions. Hydrogen is fed to the reactor 2 in line 3. An alkanol, such as methanol, is added in line 4. This may be fresh methanol or may be methanol recovered from downstream in the reaction. A product stream comprising dimethyl succinate will be removed in line 5. The stream may also include monomethyl succinate. The product stream may be passed in line 5 is passed to an ester separator 10. The dimethyl succinate is removed in line 11 as a liquid or a vapour product. It may then be passed to a hydrogenolysis reactor (not shown) where tetrahydrofuran, and/or 1,4-butanediol and/or γ-butyrolactone may be produced. Hydrogen may be supplied in line 12 to the separator 10 to assist in the separation. The monomethyl succinate may be returned in line 13 to the reactor 2.

Methanol and water are removed from the reactor 2 in line 6. It is passed to a methanol/water separator 7. The water is removed in line 8 and the methanol is recycled in line 9 where it is returned to line 4. Methanol from the subsequent hydrogenolysis reaction may be returned in line 14 to the reactor 2.

Any suitable reactor may be used for the reactor in which the hydrogenation/esterification reaction occurs. Suitable reactors include continuous stirred tank type reactors, or a fixed bed reactor with a liquid recycle. The reactor may optionally have internal or external cooling. A separate additional reaction column may be installed downstream to complete the esterification reaction which does not occur in the main reactor.

EXAMPLE 1

Maleic anhydride and 3 mol equivalents of methanol and a palladium on carbon catalyst were placed in an autoclave at 500 psig hydrogen and 190° C. The product analysis gave:

| | |
|---|---|
| Methanol | 17.12 wt % |
| Maleic anhydride | 0.51 wt % |
| Dimethyl maleate | 2.93 wt % |
| Dimethyl succinate | 55.06 wt % |
| Methoxy dimethyl succinate | 0.03 wt % |
| Monomethyl maleate | 0.13 wt % |
| Monomethyl succinate | 16.31 wt % |
| Maleic acid | 1.24 wt % |
| Fumaric acid | 0.10 wt % |
| Water | 6.52 wt % |

EXAMPLES 2 AND 3

Unless otherwise stated, all testwork was performed using a 300 ml autoclave. Hydrogen was used as the gas to generate pressure. Water was analysed using a Karl Fischer Aquapal. GC analysis was by FID using Regisil to allow for acids analysis.

EXAMPLE 2—AUTOCATALYTIC ESTERIFICATION STAGE 1

To the autoclave was charged succinic acid (40 g, 0.34 mol) and methanol (21.7 g, 0.68 mol, 2 eqv). The vessel was pressurised to 500 psig and heated to 190° C. 1 hour then cooled and discharged. The product was analysed by dissolving 50 mg of the sample in Regisil (500 mg) and acetonitrile (250 mg) then analysed using FID GC.

Using the previously described Regisil method the light components (methanol and water) were removed by crude flash distillation at 150° C. under ambient pressure.

EXAMPLE 3

50 g, 0.5 mol maleic anhydride, 49 g, 1.53 mol, 3 eqv methanol, 1 g, equivalent to 0.32 g, 0.6 wt % palladium-carbon paste were charged to the autoclave. The vessel was sealed and then pressurised to 300 psig with hydrogen and heated to 190° C. The internal temperature of the vessel was recorded with time and, to ensure that any exotherm above the desired maximum temperature was monitored, the cooling system was turned off.

The results indicated that, although the rate of temperature increase did go up, the temperature did not exceed the maximum operating parameter. Analysis of the product showed significant conversion of the maleate species to succinate with (methanol free) selectivity to mono methyl maleate and mono maleate succinate of 7.28 mol % and 11.08 mol % respectively. Selectivity to di-methyl maleate and dimethyl succinate were 3.59 mol % and 26.41 mol % respectively.

The results are set out in the following table.

| Run Number | 1208-04 |
|---|---|
| Temperature, ° C. | 190 |
| RT at 190° C., min | 10 |
| GC Analysis, wt % | |
| MeOH | 24.87 |
| MAH | 0.38 |
| DMM | 4.41 |
| DMF | 3.70 |
| DMS | 32.90 |
| DMC | 0.04 |
| MeODMS | 0.06 |
| MMM | 8.07 |
| MMS | 12.48 |
| MMF | 4.48 |
| MMC | 0.20 |
| HO-DMS | 0.02 |
| MAC | 0.47 |
| SAC | 0.88 |
| FAC | 0.44 |
| Water | 6.47 |

The invention claimed is:

1. A process for the production of dialkyl succinate from a feedstock comprising maleic anhydride, said process comprising the steps of:
   (a) providing the feed in the liquid phase to a reactor operated at a temperature of at least about 150° C.;
   (b) contacting said feed with hydrogen at a pressure of about 300 psig to about 900 psig in the presence of an acid tolerant catalyst and methanol wherein at least some of the carbon carbon double bonds of the maleic anhydride are hydrogenated to form succinic acid and that the heat generated promotes esterification to dialkyl succinate in situ; and
   (c) recovering a stream comprising dialkyl succinate from the reactor.

2. The process according to claim 1 wherein the feed to the reactor comprises at least 90% maleic anhydride.

3. The process according to claim 1 wherein the reaction is carried out at a temperature of from about 150° C. to about 240° C.

4. The process according to claim 1 wherein the esterification reaction is carried out in the absence of a catalyst.

5. The process according to claim 1 wherein an esterification catalyst is used.

6. The process according to claim 5 wherein a combined catalyst is used.

7. The process according to claim 1 wherein the saturation reaction is carried out at a temperature in the range of from about 150° C. to about 240° C.

8. The process according to claim 1 wherein the succinate produced is recycled to the reactor.

* * * * *